(12) United States Patent
Miklos et al.

(10) Patent No.: US 11,753,670 B1
(45) Date of Patent: Sep. 12, 2023

(54) CELL-FREE PROTEIN SYNTHESIS METHODS USING LYSATES OF YERSINIA PESTIS

(71) Applicant: U.S. Army Combat Capabilities Development Command, Chemical Biological Center, APG, MD (US)

(72) Inventors: Aleksandr E. Miklos, Baldwin, MD (US); Katherine A. Rhea, Edgewood, MD (US); Nathan D. McDonald, Newark, DE (US); Stephanie D. Cole, Forest Hill, MD (US); Patricia E. Buckley, Parkville, MD (US)

(73) Assignee: The United States of America as Represented by the Secretary of the Army, Washington, DC (US)

( * ) Notice: Subject to any disclaimer, the term of this patent is extended or adjusted under 35 U.S.C. 154(b) by 0 days.

(21) Appl. No.: 17/862,495

(22) Filed: Jul. 12, 2022

Related U.S. Application Data

(60) Provisional application No. 63/224,976, filed on Jul. 23, 2021.

(51) Int. Cl.
*C12P 21/02* (2006.01)
*C12N 9/12* (2006.01)
*C12N 15/74* (2006.01)

(52) U.S. Cl.
CPC ............ *C12P 21/02* (2013.01); *C12N 9/1247* (2013.01); *C12N 15/74* (2013.01); *C12Y 207/07006* (2013.01); *C12N 2800/101* (2013.01)

(58) Field of Classification Search
None
See application file for complete search history.

(56) References Cited

PUBLICATIONS

Sun et al. (Protocols for Implementing an *Escherichia coli* Based TX-TL Cell-Free Expression System for Synthetic Biology, Journal of Visualized Experiments, Sep. 2013, (79): e50762, pp. 1-14).*

* cited by examiner

*Primary Examiner* — Manjunath N Rao
*Assistant Examiner* — Jae W Lee
(74) *Attorney, Agent, or Firm* — Ulysses John Biffoni

(57) ABSTRACT

Disclosed are compositions, methods, and kits for performing cell-free RNA transcription and/or cell-free protein synthesis (CFPS). The disclosed compositions, methods, and kits include or utilize components prepared from *Yersinia pestis* species such as cellular extracts from *Yersinia pestis*.

19 Claims, 3 Drawing Sheets

US 11,753,670 B1

CELL-FREE PROTEIN SYNTHESIS METHODS USING LYSATES OF YERSINIA PESTIS

PRIORITY CLAIM

Figure 1:
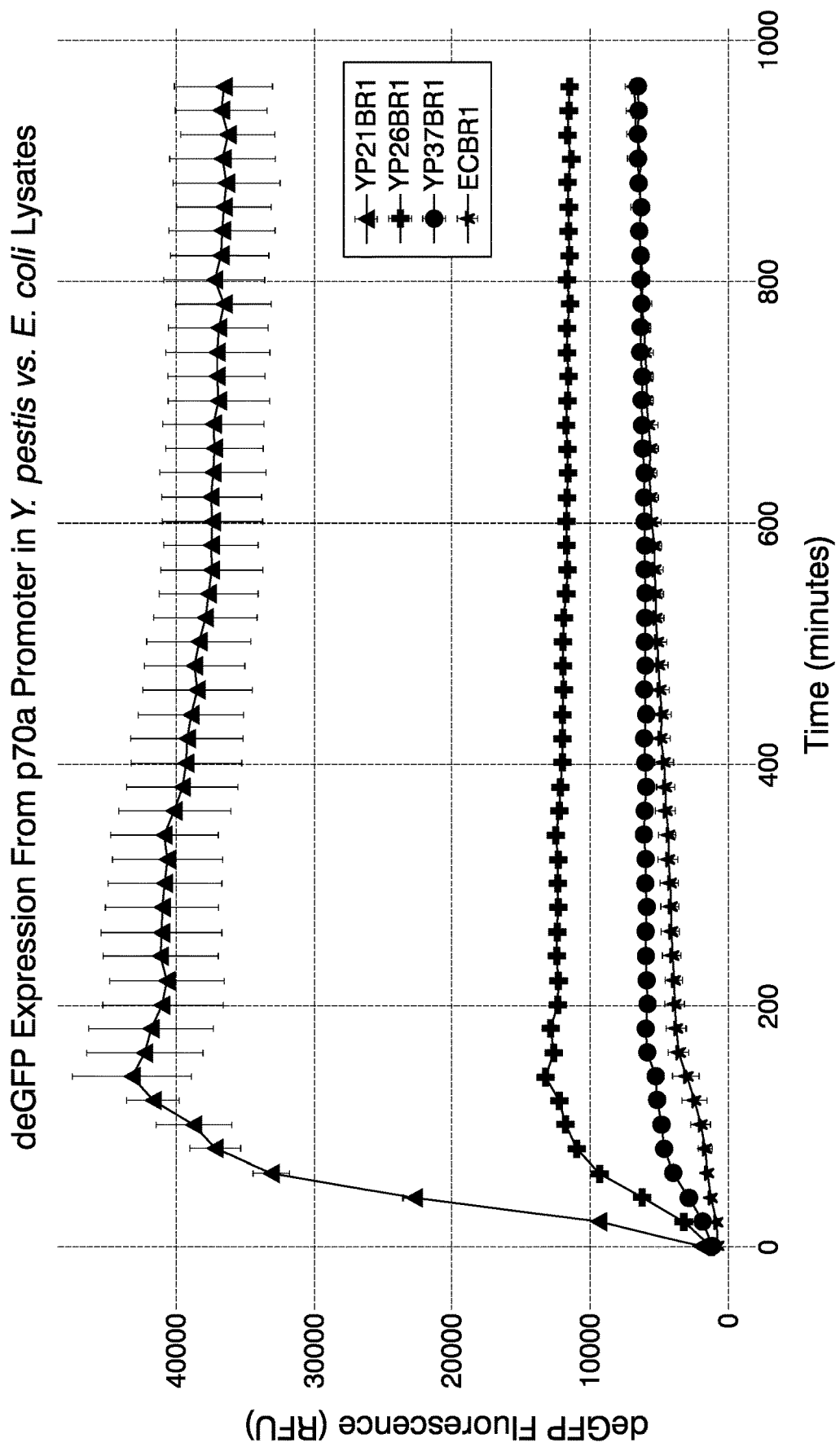
Figure 2:
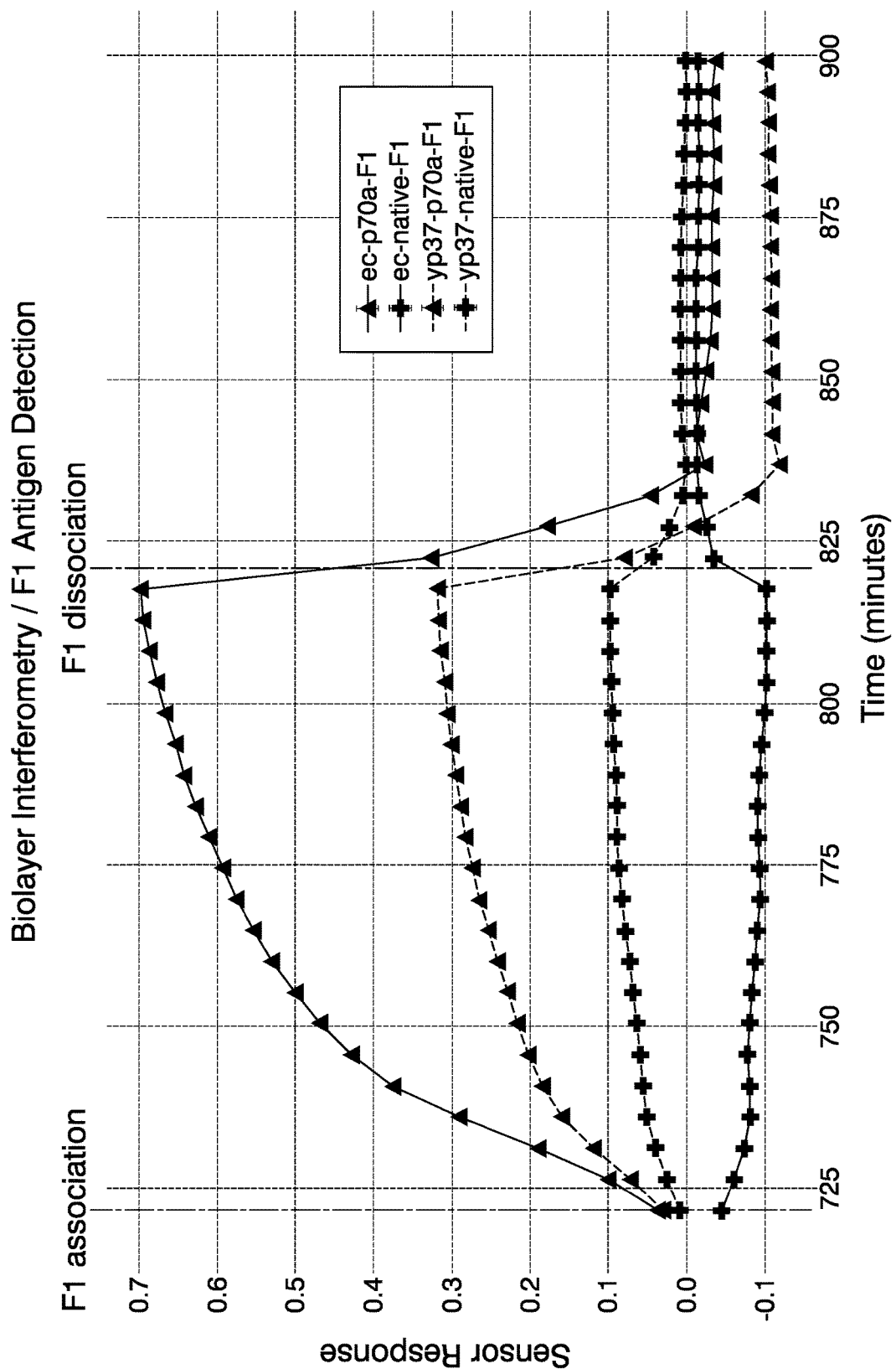
Figure 3:
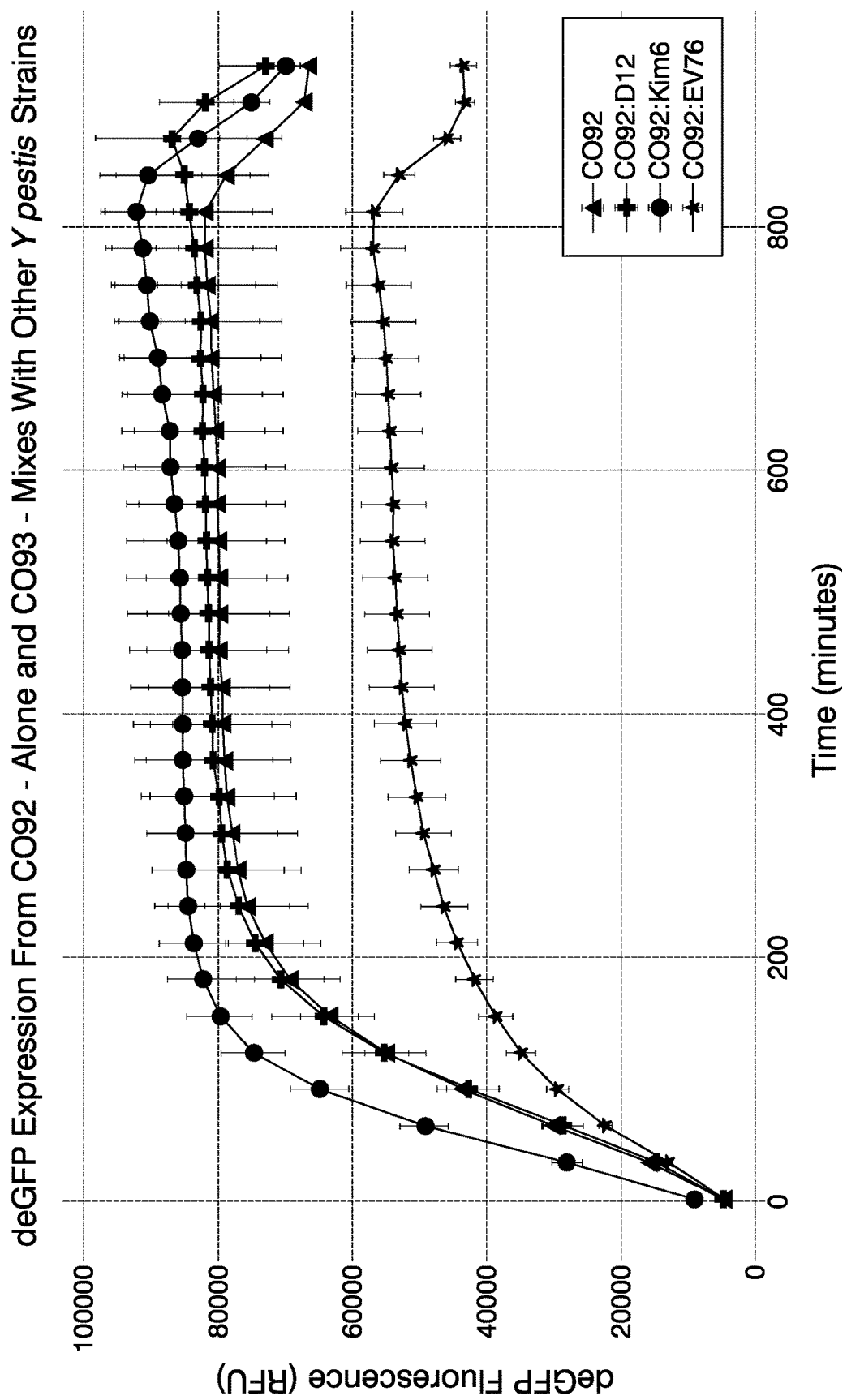

This application claims the benefit of priority from U.S. Provisional Patent Application Ser. No. 63/224,976 filed Jul. 23, 2021.

GOVERNMENT INTEREST

The invention described herein may be manufactured, used, and licensed by or for the United States Government.

FIELD OF THE INVENTION

The present invention is directed towards methods and kits of cell free protein synthesis using prokaryotic cell lysates.

BACKGROUND OF THE INVENTION

"Cell free systems" are essentially the filtered contents of lysed cells, which, if prepared with suitable methods and provided with the appropriate energy chemicals and precursors, will perform some of the essential functions of the original cells (most commonly transcribing DNA to RNA and translating RNA to protein)—without intact or viable cells.

The lack of intact cells, or membrane thereof around the cellular machinery, enables DNA into the mix and extracting products thereof is much easier. Therefore, these systems are popular in screening engineered biological components for function and evaluating synthetic biological circuits and schemes—there is no cloning and no growing up a population of your modified cells required—DNA of interest can be rapidly characterized simply by mixing with a lysate system and screening for products.

The use of cell-free protein synthesis systems ("CFPS") to rapidly prototype engineered biological parts and circuits has become a standard technique. These systems consist of cellular extract containing the macromolecules necessary for transcription and translation along with a formulated energy cocktail containing the precursors and energy mixtures that these processes consume. The function of the end product is most typically the synthesis of a protein, but also the production of RNA or the establishment of circuits or metabolic pathways have been described.

Cell-free lysates were originally used as a means to study transcription and translation prior to recombinant approaches. Lysates are resurgent due to their ability to produce difficult protein targets and their utility in synthetic biology applications: Cell-free systems serve as a breadboard of sorts where changes can be made quickly, and results can be assessed before undertaking the additional effort of establishing those changes in an organism. These systems have also found utility in the production of high-value biological products and sensing schemes in austere settings as the lysates can be preserved more readily than live organisms and the systems are generally easy to use once created.

The majority of CFPS are based on lysates from various strains of *E. coli*. Diversifying the available backgrounds on which CFPS are built is of interest to those seeking expanded or novel functions in CFPS for biotechnological purposes.

Lysates have also been made from other bacteria such as *Vibrio natriegens* in US20210171584A1 by Jewett et al., and various plant, insect, and mammalian cells. Each system tends to have a specific advantage, usually in the types of protein each system can produce.

Despite the emergence of cell-free systems as a prominent research tool for fundamental and applied biology, the vast majority of previous efforts have focused on a select few model systems such as *Escherichia coli, Saccharomyces cerevisiae*, and Chinese Hamster Ovary cells, among others. However, cell-free systems composed of extracts derived from relevant chassis organisms that better mimic the natural physicochemical environment, might enhance predictive power for synthetic biology applications. Further, for studying BSL-2 strains, CFPS can potentially reduce risks associated with laboratory operations on pathogenic organisms. This idea motivates the development of new cell-free systems. In this context, several new CFPS systems have been developed based upon *Yersinia pestis.*

SUMMARY OF THE INVENTION

The present invention is directed to compositions, methods, and kits for performing cell-free RNA transcription and/or cell-free protein synthesis (CFPS). More specifically, the present invention relates to compositions, methods, and kits for performing cell-free RNA transcription and/or performing cell-free protein synthesis (CFPS) that include or utilize components prepared from naturally occurring or recombinant *Yersinia* species such as cellular extracts from *Yersinia pestis.*

BRIEF DESCRIPTION OF DRAWINGS

FIG. 1 illustrates deGFP expression from p70a promoter in *Y. pestis* vs. *E. coli* lysates.

FIG. 2 illustrates biolayer interferometry/F1 Antigen Detection in in *Y. pestis* vs. *E. coli* lysates.

FIG. 3 illustrates deGFP Expression from $CO92^-$ Alone and $CO92^-$ mixed with other *Y. pestis* strains.

DETAILED DESCRIPTION OF THE INVENTION

Definition of Terminology

As used herein, a "polymerase" refers to an enzyme that catalyzes the polymerization of nucleotides. "DNA polymerase" catalyzes the polymerization of deoxyribonucleotides. Known DNA polymerases include, for example, *Pyrococcus furiosus* (Pfu) DNA polymerase, *E. coli* DNA polymerase I, T7 DNA polymerase and *Thermus aquaticus* (Taq) DNA polymerase, among others. "RNA polymerase" catalyzes the polymerization of ribonucleotides. The foregoing examples of DNA polymerases are also known as DNA-dependent DNA polymerases. RNA-dependent DNA polymerases also fall within the scope of DNA polymerases. Reverse transcriptase, which includes viral polymerases encoded by retroviruses, is an example of an RNA-dependent DNA polymerase. Known examples of RNA polymerase ("RNAP") include, for example, RNA polymerases of bacteriophages (e.g., T3 RNA polymerase, T7 RNA polymerase, SP6 RNA polymerase), and *E. coli* RNA polymerase, among others. The foregoing examples of RNA polymerases are also known as DNA-dependent RNA polymerase. The polymerase activity of any of the above enzymes can be determined by means well known in the art.

The term "promoter" refers to a cis-acting DNA sequence that directs RNA polymerase and other trans-acting transcription factors to initiate RNA transcription from the DNA template that includes the cis-acting DNA sequence.

As used herein, the term "sequence defined biopolymer" refers to a biopolymer having a specific primary sequence. A sequence defined biopolymer can be equivalent to a genetically encoded defined biopolymer in cases where a gene encodes the biopolymer having a specific primary sequence. As used herein, "expression" refers to the process by which a polyribonucleotide (typically but not exclusively mRNA) is transcribed from a DNA template (such as into and mRNA or other RNA transcript) and/or the process by which a transcribed mRNA is subsequently translated into peptides, polypeptides, or proteins. Transcripts and encoded polypeptides may be collectively referred to as "gene product." If the polynucleotide is derived from genomic DNA, expression may include splicing of the mRNA in a eukaryotic cell.

As used herein, "expression template" refers to a polynucleotide sequence that gives rise to a polypeptide/protein sequence via direct translation (in the case of RNA) and/or via transcription and translation (in the case of DNA). Suitable sources of DNA for use as a nucleic acid for an expression template include genomic DNA, cDNA and RNA that can be converted into cDNA. Genomic DNA, cDNA and RNA can be chemically or enzymatically synthesized, or from any biological source, such as a tissue sample, a biopsy, a swab, sputum, a blood sample, a fecal sample, a urine sample, a scraping, among others. The genomic DNA, cDNA and RNA can be from host cell or virus origins and from any species, including extant and extinct organisms. As used herein, "expression template" and "transcription template" have the same meaning and are used interchangeably.

In certain exemplary embodiments, vectors are expression vectors that contain a nucleic acid encoding one or more rRNAs or reporter polypeptides and/or proteins as described herein. As used herein, the term "vector" refers to a nucleic acid molecule capable of transporting another nucleic acid to which it has been linked. One type of vector is a "plasmid," which refers to a circular double stranded DNA loop into which additional DNA segments can be ligated. Such vectors are referred to herein as "expression vectors." In general, expression vectors of utility in recombinant DNA techniques are often in the form of plasmids. In the present specification, "plasmid" and "vector" can be used interchangeably. However, the disclosed methods and compositions are intended to include such other forms of expression vectors, such as viral vectors (e.g., replication defective retroviruses, adenoviruses, and adeno-associated viruses), which serve equivalent functions.

In certain exemplary embodiments, the recombinant expression vectors comprise a nucleic acid sequence (e.g., a nucleic acid sequence encoding one or more rRNAs or reporter polypeptides and/or proteins described herein) in a form suitable for expression of the nucleic acid sequence in one or more of the methods described herein, which means that the recombinant expression vectors include one or more regulatory sequences which is operatively linked to the nucleic acid sequence to be expressed. Within a recombinant expression vector, "operably linked" is intended to mean that the nucleotide sequence encoding one or more rRNAs or reporter polypeptides and/or proteins described herein is linked to the regulatory sequence(s) in a manner which allows for expression of the nucleotide sequence (e.g., in an in vitro rRNA assembly, transcription and/or translation system). The term "regulatory sequence" is intended to include promoters, enhancers, and other expression control elements (e.g., polyadenylation signals). Such regulatory sequences are described, for example, in Goeddel; Gene Expression Technology: Methods in Enzymology 185, Academic Press, San Diego, Calif. (1990).

The polynucleotide sequences useful herein may be present in expression vectors. For example, the vectors may comprise: (a) a polynucleotide encoding an ORF of a protein; (b) a polynucleotide that expresses an RNA that directs RNA-mediated binding, nicking, and/or cleaving of a target DNA sequence; and both (a) and (b). The polynucleotide present in the vector may be operably linked to a prokaryotic or eukaryotic promoter. "Operably linked" refers to the situation in which a first nucleic acid sequence is placed in a functional relationship with a second nucleic acid sequence. For instance, a promoter is operably linked to a coding sequence if the promoter affects the transcription or expression of the coding sequence. Operably linked DNA sequences may be in close proximity or contiguous and, where necessary to join two protein coding regions, in the same reading frame. Vectors contemplated herein may comprise a heterologous promoter (e.g., a eukaryotic or prokaryotic promoter) operably linked to a polynucleotide that encodes a protein. A "heterologous promoter" refers to a promoter that is not the native or endogenous promoter for the protein or RNA that is being expressed. Vectors as disclosed herein may include plasmid vectors.

The disclosed methods, devices, kits, and components may be utilized to synthesize proteins, polypeptides, and/or peptides. As used herein, the terms "protein" or "polypeptide" or "peptide" may be used interchangeable to refer to a polymer of amino acids. Typically, a "polypeptide" or "protein" is defined as a longer polymer of amino acids, of a length typically of greater than 50, 60, 70, 80, 90, or 100 amino acids. A "peptide" is defined as a short polymer of amino acids, of a length typically of 50, 40, 30, 20 or less amino acids.

As used herein, the terms "peptide," "polypeptide," and "protein," refer to molecules comprising a chain or polymer of amino acid residues joined by amide linkages. The term "amino acid residue," includes but is not limited to amino acid residues contained in the group consisting of alanine (Ala or A), cysteine (Cys or C), aspartic acid (Asp or D), glutamic acid (Glu or E), phenylalanine (Phe or F), glycine (Gly or G), histidine (His or H), isoleucine (Ile or I), lysine (Lys or K), leucine (Leu or L), methionine (Met or M), asparagine (Asn or N), proline (Pro or P), glutamine (Gln or Q), arginine (Arg or R), serine (Ser or S), threonine (Thr or T), valine (Val or V), tryptophan (Trp or W), and tyrosine (Tyr or Y) residues. The term "amino acid residue" also may include nonstandard, noncanonical, or unnatural amino acids, which optionally may include amino acids other than any of the following amino acids: alanine, cysteine, aspartic acid, glutamic acid, phenylalanine, glycine, histidine, isoleucine, lysine, leucine, methionine, asparagine, proline, glutamine, arginine, serine, threonine, valine, tryptophan, and tyrosine residues. The term "amino acid residue" may include alpha-, beta-, gamma-, and delta-amino acids.

In some embodiments, the term "amino acid residue" may include nonstandard, noncanonical, or unnatural amino acid residues. Examples of this group include but are not limited to homocysteine, 2-Aminoadipic acid, N-Ethylasparagine, 3-Aminoadipic acid, Hydroxylysine, β-alanine, β-Aminopropionic acid, allo-Hydroxylysine acid, 2-Aminobutyric acid, 3-Hydroxyproline, 4-Aminobutyric acid, 4-Hydroxyproline, piperidinic acid, 6-Aminocaproic acid, Isodesmosine, 2-Aminoheptanoic acid, allo-Isoleucine, 2-Aminoisobutyric acid, N-Methylglycine, sarcosine, 3-Aminoisobutyric acid, N-Methylisoleucine, 2-Aminopimelic acid, 6-N-Methyllysine, 2,4-Diaminobutyric acid, N-Methylvaline, Desmosine, Norvaline, 2,2'-Diaminopimelic acid, Norleucine, 2,3-Diaminopropionic acid, Ornithine, and N-Ethylglycine. The term "amino acid residue" may include L isomers or D isomers of any of the aforementioned amino acids.

Other examples of nonstandard, noncanonical, or unnatural amino acids include, but are not limited, to a p-acetyl-L-phenylalanine, a p-iodo-L-phenylalanine, an O-methyl-L-tyrosine, a p-propargyloxyphenylalanine, a p-propargylphenylalanine, an L-3-(2-naphthyl)alanine, a 3-methylphenylalanine, an O-4-allyl-L-tyrosine, a 4-propyl-L-tyrosine, a tri-O-acetyl-GlcNAcpβ-serine, an L-Dopa, a fluorinated phenylalanine, an isopropyl-L-phenylalanine, a p-azido-L-phenylalanine, a p-acyl-L-phenylalanine, a p-benzoyl-L-phenylalanine, an L-phosphoserine, a phosphonoserine, a phosphonotyrosine, a p-bromophenylalanine, a p-amino-L-phenylalanine, an isopropyl-L-phenylalanine, an unnatural analogue of a tyrosine amino acid; an unnatural analogue of a glutamine amino acid; an unnatural analogue of a phenylalanine amino acid; an unnatural analogue of a serine amino acid; an unnatural analogue of a threonine amino acid; an unnatural analogue of a methionine amino acid; an unnatural analogue of a leucine amino acid; an unnatural analogue of a isoleucine amino acid; an alkyl, aryl, acyl, azido, cyano, halo, hydrazine, hydrazide, hydroxyl, alkenyl, alkynl, ether, thiol, sulfonyl, seleno, ester, thioacid, borate, boronate, 18ufa18hor, phosphono, phosphine, heterocyclic, enone, imine, aldehyde, hydroxylamine, keto, or amino substituted amino acid, or a combination thereof; an amino acid with a photoactivatable cross-linker; a spin-labeled amino acid; a fluorescent amino acid; a metal binding amino acid; a metal-containing amino acid; a radioactive amino acid; a photocaged and/or photoisomerizable amino acid; a biotin or biotin-analogue containing amino acid; a keto containing amino acid; an amino acid comprising polyethylene glycol or polyether; a heavy atom substituted amino acid; a chemically cleavable or photocleavable amino acid; an amino acid with an elongated side chain; an amino acid containing a toxic group; a sugar substituted amino acid; a carbon-linked sugar-containing amino acid; a redox-active amino acid; an α-hydroxy containing acid; an amino thio acid; an α,α disubstituted amino acid; a β-amino acid; a γ-amino acid, a cyclic amino acid other than proline or histidine, and an aromatic amino acid other than phenylalanine, tyrosine or tryptophan.

As used herein, a "peptide" is defined as a short polymer of amino acids, of a length typically of 20 or less amino acids, and more typically of a length of 12 or less amino acids (Garrett & Grisham, Biochemistry, 2nd edition, 1999, Brooks/Cole, 110). In some embodiments, a peptide as contemplated herein may include no more than about 2, 3, 4, 5, 6, 7, 8, 9, 10, 11, 12, 13, 14, 15, 16, 17, 18, 19, or 20 amino acids. A polypeptide, also referred to as a protein, is typically of length 100 amino acids (Garrett & Grisham, Biochemistry, 2nd edition, 1999, Brooks/Cole, 110). A polypeptide, as contemplated herein, may comprise, but is not limited to, 100, 101, 102, 103, 104, 105, about 110, about 120, about 130, about 140, about 150, about 160, about 170, about 180, about 190, about 200, about 210, about 220, about 230, about 240, about 250, about 275, about 300, about 325, about 350, about 375, about 400, about 425, about 450, about 475, about 500, about 525, about 550, about 575, about 600, about 625, about 650, about 675, about 700, about 725, about 750, about 775, about 800, about 825, about 850, about 875, about 900, about 925, about 950, about 975, about 1000, about 1100, about 1200, about 1300, about 1400, about 1500, about 1750, about 2000, about 2250, about 2500 or more amino acid residues.

A peptide as contemplated herein may be further modified to include non-amino acid moieties. Modifications may include but are not limited to acylation (e.g., O-acylation (esters), N-acylation (amides), S-acylation (thioesters)), acetylation (e.g., the addition of an acetyl group, either at the N-terminus of the protein or at lysine residues), formylation lipoylation (e.g., attachment of a lipoate, a C8 functional group), myristoylation (e.g., attachment of myristate, a C14 saturated acid), palmitoylation (e.g., attachment of palmitate, a C16 saturated acid), alkylation (e.g., the addition of an alkyl group, such as an methyl at a lysine or arginine residue), isoprenylation or prenylation (e.g., the addition of an isoprenoid group such as farnesol or geranylgeraniol), amidation at C-terminus, glycosylation (e.g., the addition of a glycosyl group to either asparagine, hydroxylysine, serine, or threonine, resulting in a glycoprotein). Distinct from glycation, which is regarded as a nonenzymatic attachment of sugars, polysialylation (e.g., the addition of polysialic acid), glypiation (e.g., glycosylphosphatidylinositol (GPI) anchor formation, hydroxylation, iodination (e.g., of thyroid hormones), and phosphorylation (e.g., the addition of a phosphate group, usually to serine, tyrosine, threonine, or histidine).

The proteins disclosed herein may include "wild type" proteins and variants, mutants, and derivatives thereof. As used herein the term "wild type" is a term of the art understood by skilled persons and means the typical form of an organism, strain, gene or characteristic as it occurs in nature as distinguished from mutant or variant forms. As used herein, a "variant, "mutant," or "derivative" refers to a protein molecule having an amino acid sequence that differs from a reference protein or polypeptide molecule. A variant or mutant may have one or more insertions, deletions, or substitutions of an amino acid residue relative to a reference molecule. A variant or mutant may include a fragment of a reference molecule. For example, a mutant or variant molecule may one or more insertions, deletions, or substitution of at least one amino acid residue relative to a reference polypeptide.

Regarding proteins, the amino acid sequences of variants, mutants, or derivatives as contemplated herein may include conservative amino acid substitutions relative to a reference amino acid sequence. For example, a variant, mutant, or derivative protein may include conservative amino acid substitutions relative to a reference molecule. "Conservative amino acid substitutions" are those substitutions that are a substitution of an amino acid for a different amino acid where the substitution is predicted to interfere least with the properties of the reference polypeptide. In other words, conservative amino acid substitutions substantially conserve the structure and the function of the reference polypeptide. The following table provides a list of exemplary conservative amino acid substitutions which are contemplated herein:

| Original Residue | Conservative Substitution |
| --- | --- |
| Ala | Gly, Ser |
| Arg | His, Lys |
| Asn | Asp, Gln, His |
| Asp | Asn, Glu |

-continued

| Original Residue | Conservative Substitution |
|---|---|
| Cys | Ala, Ser |
| Gln | Asn, Glu, His |
| Glu | Asp, Gln, His |
| Gly | Ala |
| His | Asn, Arg, Gln, Glu |
| Ile | Leu, Val |
| Leu | Ile, Val |
| Lys | Arg, Gln, Glu |
| Met | Leu, Ile |
| Phe | His, Met, Leu, Trp, Tyr |
| Ser | Cys, Thr |
| Trp | Phe, Tyr |
| Tyr | His, Phe, Trp |
| Val | Ile, Leu, Thr |

Conservative amino acid substitutions generally maintain (a) the structure of the polypeptide backbone in the area of the substitution, for example, as a beta sheet or alpha helical conformation, (b) the charge or hydrophobicity of the molecule at the site of the substitution, and/or (c) the bulk of the side chain. Non-conservative amino acids typically disrupt (a) the structure of the polypeptide backbone in the area of the substitution, for example, as a beta sheet or alpha helical conformation, (b) the charge or hydrophobicity of the molecule at the site of the substitution, and/or (c) the bulk of the side chain.

The disclosed proteins, mutants, variants, or described herein may have one or more functional or biological activities exhibited by a reference polypeptide (e.g., one or more functional or biological activities exhibited by wild-type protein).

The disclosed proteins may be substantially isolated or purified. The term "substantially isolated or purified" refers to proteins that are removed from their natural environment, and are at least 60% free, preferably at least 75% free, and more preferably at least 90% free, even more preferably at least 95% free from other components with which they are naturally associated.

The proteins disclosed herein may be expressed from a "translation template." As used herein, "translation template" refers to an RNA product of transcription from an expression template that can be used by ribosomes to synthesize polypeptides or proteins.

The proteins disclosed herein may be expressed in a "reaction mixture." The term "reaction mixture," as used herein, refers to a solution containing reagents necessary to carry out a given reaction. A reaction mixture is referred to as complete if it contains all reagents necessary to perform the reaction. Components for a reaction mixture may be stored separately in separate container, each containing one or more of the total components. Components may be packaged separately for commercialization and useful commercial kits may contain one or more of the reaction components for a reaction mixture.

Cell Free Protein Synthesis

Cell-free protein synthesis (CFPS) and methods for making cell extracts for use in CFPS are known in the art.

The present inventive compositions may include platforms for preparing a sequence defined biopolymer of protein in vitro. The platforms for preparing a sequence defined polymer or protein in vitro comprises a cellular extract from an organism, and in particular a species of Yersinia, such as Yersinia pestis. Because CFPS exploits an ensemble of catalytic proteins prepared from the crude lysate of cells, the cell extract (whose composition is sensitive to growth media, lysis method, and processing conditions) is an important component of extract based CFPS reactions. A variety of methods exist for preparing an extract competent for cell-free protein synthesis, including those disclosed in U.S. Published Application No. 20140295492, published on Oct. 2, 2014, which is incorporated by reference.

The platform may comprise an expression template, a translation template, or both an expression template and a translation template. The expression template serves as a substrate for transcribing at least one RNA that can be translated into a sequence defined biopolymer (e.g., a polypeptide or protein). The translation template is an RNA product that can be used by ribosomes to synthesize the sequence defined biopolymer. In certain embodiments the platform comprises both the expression template and the translation template. In certain specific embodiments, the platform may be a coupled transcription/translation ("TX/TL") system where synthesis of translation template and a sequence defined biopolymer from the same cellular extract.

The platform may comprise one or more polymerases capable of generating a translation template from an expression template. The polymerase may be supplied exogenously or may be supplied from the organism used to prepare the extract. In certain specific embodiments, the polymerase is expressed from a plasmid present in the organism used to prepare the extract and/or an integration site in the genome of the organism used to prepare the extract.

The platform may comprise an orthogonal translation system. An orthogonal translation system may comprise one or more orthogonal components that are designed to operate parallel to and/or independent of the organism's orthogonal translation machinery. In certain embodiments, the orthogonal translation system and/or orthogonal components are configured to incorporation of unnatural amino acids. An orthogonal component may be an orthogonal protein or an orthogonal RNA. In certain embodiments, an orthogonal protein may be an orthogonal synthetase. In certain embodiments, the orthogonal RNA may be an orthogonal tRNA or an orthogonal rRNA. An example of an orthogonal rRNA component has been described in U.S. Published Application Nos. 20170073381 and 20160060301, the contents of which are incorporated by reference in their entireties. In certain embodiments, one or more orthogonal components may be prepared in vivo or in vitro by the expression of an oligonucleotide template. The one or more orthogonal components may be expressed from a plasmid present in the genomically recoded organism, expressed from an integration site in the genome of the genetically recoded organism, co-expressed from both a plasmid present in the genomically recoded organism and an integration site in the genome of the genetically recoded organism, express in the in vitro transcription and translation reaction, or added exogenously as a factor (e.g., a orthogonal tRNA or an orthogonal synthetase added to the platform or a reaction mixture.

Platforms Comprising Extracts from Yersinia Species

Yersinia pestis, the causative agent of the bubonic plague, exists in a unique life cycle in which it is exposed to a variety of hosts and must respond to a series of environmental cues. One of the major abiotic stimuli that Y. pestis has adapted to is fluctuation in temperature. Similar to other pathogens, the expression of many virulence factors of Y. Pestis are induced upon an increase in temperature, along with major shifts in metabolism.

The present inventive compositions (or systems) include platforms for preparing a sequence defined biopolymer or protein in vitro, where the platform comprising a cellular extract prepared from a cell culture of a species of *Yersinia*. In particular, the species of *Yersinia* may include *Yersinia pestis*.

The species of *Yersinia* may be a naturally occurring isolate (i.e., a wild-type species), or the species of *Yersinia* may be engineered. For example, the species of *Yersinia* may be engineered genetically to be deficient in a negative effector for cell-free protein synthesis (CFPS), for example via a knock-out mutation. Negative effectors for CFPS have been defined for *E. coli* and may include, but are not limited to, endA, lon, mazF, ompT, ma, rnb, glpK, gor, gshA, tnaA, me, gdhA, sdaA, sdaB, speA, waaL, and any combination thereof which are well known in the prior art.

The species of *Yersinia pestis* contemplated herein may be engineered to be deficient in a gene encoding the corresponding homolog of any of *E. coli* endA, mazF, ma, rnb, me, gor, lon, ompT, gdhA, gshA, sdaA, sdaB, speA, WaaL, tnaA, glpK, and any combination thereof. Specifically, the species of *Yersinia* contemplated herein may be deficient in a gene which encodes the corresponding homolog of any of *E. coli* endA, mazF, ma, rnb, me, gor, Ion, ompT, gdhA, gshA, sdaA, sdaB, speA, WaaL, tnaA, glpK, which homolog has at least about 20%, 30%, 40%, 50%, 60%, 70%, 75%, 80%, 85%, 90%, 95%, 96%, 97%, 98%, or 99% amino acid sequence identity to one or more of endA, Ion, mazF, ompT, ma, mb, glpK, gor, gshA, tnaA, me, gdhA, sdaA, sdaB, speA, WaaL, and any combination thereof.

In some embodiments, the species of *Yersinia* contemplated herein may be engineered to be deficient in one or more of Vnat_endA, Vnat_lon, Vnat_rnb, Vnat_glpK, Vnat_gor, Vnat_gshA, Vnat_tnaA, or any combination thereof.

In addition, or in the alternative, the species of *Yersinia* may be engineered to express an upregulated gene product that is a positive effector for CFPS. Positive effectors for CFPS have been defined for *E. coli* and may include, but are not limited to ackA, ndk, pykF, cdd, dsbC, dnaK, dnaJ, crpE, tig, groS, groL, infA, infB, fusA, efp, lepA, tufB, hs1R, ffr, and any combination thereof. The species of *Yersinia* may be engineered genomically, for example by recombinantly introducing heterologous DNA into the genome of the species of *Yersinia*, and or the species of *Yersinia* may be engineered by introducing an episomal vector (e.g., a plasmid) to the species of *Yersinia* in order to create an engineered species of *Yersinia* that expresses an upregulated gene product that is the corresponding homolog of any of *E. coli* ackA, ndk, pykF, cdd, dsbC, dnaK, dnaJ, crpE, tig, groS, groL, infA, infB, fusA, efp, lepA, tufB, hs1R, ffr, and any combination thereof. For example, the species of *Yersinia* contemplated herein may be engineered to express an upregulated gene product that has an amino acid sequence having at least about 20%, 30%, 40%, 50%, 60%, 70%, 75%, 80%, 85%, 90%, 95%, 96%, 97%, 98%, or 99% amino acid sequence identity to one or more of *E. coli* ackA, ndk, pykF, cdd, dsbC, dnaK, dnaJ, crpE, tig, groS, groL, infA, infB, fusA, efp, lepA, tufB, hs1R, ffr, and any combination thereof.

The species of *Yersinia* may be engineered to be deficient specifically in a release factor of translation. Release factors for translation may include but are not limited to release factor 1 (RF-1).

The species of *Yersinia* may be engineered to express a non-native or heterologous RNA polymerase, for example, by recombinantly introducing heterologous DNA encoding the RNA polymerase into the genome of the species of *Yersinia*, and or the species of *Yersinia* may be engineered by introducing an episomal vector that expresses the RNA polymerase (e.g., a plasmid) to the species of *Yersinia*. Suitable RNA polymerases may include but are not limited to T7 RNA polymerase.

The cellular extract of the platform is prepared from a cell culture of a species of *Yersinia*. In some embodiments, the cell culture is in stationary phase. In some embodiments, stationary phase may be defined as the cell culture having an OD600 of greater than about 3.0, 3.5, 4.0, 4.5, 5.0, 5.5, 6.0, 6.5, 7.0, 7.5, 8.0, or having an OD600 within a range bounded by any of these values.

The cell extract may be prepared by lysing the cells of the cell culture and isolating a fraction from the lysed cells. For example, the cell extract may be prepared by lysing the cells of the cell culture and subjecting the lysed cells to centrifugal force, and isolating a fraction after centrifugation (e.g., where the S12 fraction and/or S30 fraction is isolated).

The platforms disclosed herein may include additional components, for example, one or more components for performing CFPS. Components may include, but are not limited to amino acids which optionally may include non-canonical amino acids, NTPs, salts (e.g., sodium salts, potassium salts, and/or magnesium salts), cofactors (e.g., nicotinamide adenine dinucleotide (NAD) and/or coenzyme-A (CoA)), an energy source and optionally an energy source comprising a phosphate group (e.g., phosphoenol pyruvate (PEP), ATP, or creatine phosphate), a translation template (e.g., a non-native mRNA that is translated in the platform) and/or a transcription template (e.g., a template DNA for synthesizing a non-native mRNA that is translated in the platform), and any combination thereof.

In some embodiments, the platform may comprise an energy source and optionally an energy source comprising a phosphate group (e.g., phosphoenol pyruvate (PEP), ATP, or creatine phosphate), where the energy source is present in the platform at a concentration of greater than about 30 mM, 40 mM, 50 mM, 60 mM, 70 mM, 80 mM, or 90 mM (preferably greater than about 67 mM), but less than about 100 mM, or within a concentration range bounded by of these values.

In some embodiments, the platform further comprises a source of potassium ($K^+$, such as a potassium salt such as potassium glutamate), wherein the platform comprises potassium at a concentration greater than about 50 mM, 100 mM, 150 mM, 200 mM, 250 mM, 300 mM, 350 mM, 400 mM, or 450 mM; preferably about 300 mM but less than about 500 mM, or within a concentration range bounded by of these values, The disclosed platforms and cell extracts may be utilized in methods for preparing a sequence defined biopolymer or protein in vitro. The disclosed methods typically include translating in vitro a translation template (e.g., mRNA) encoding the sequence defined biopolymer or protein in the platform of any of the foregoing claims. Optionally, the disclosed methods may include transcribing a transcription template (e.g., DNA) in the platform to provide the translation template.

The disclosed methods may be performed under conditions that are suitable for cellular extracts prepared from a species of *Yersinia*. In some embodiments, the disclosed methods are performed at a temperature between about 20 to 40° C., and preferably at a temperature of about 21 to 37° C.

The disclosed methods may be performed to synthesize any sequence defined biopolymer or protein. In some embodiments, the sequence defined polymer or protein is a therapeutic protein and/or the method may utilize to identify therapeutic proteins or biomaterials by translating a library of transcription templates. In some embodiments, the disclosed methods may be performed to optimize in vitro translation conditions for a cellular extract prepared from a species of Yersinia.

Kits also are contemplated herein. In some embodiments, the contemplated kits comprise as components: (a) a cellular extract prepared from a cell culture of a species of *Yersinia* (e.g., *Yersinia pestis*); and (b) a reaction mixture for translating an mRNA. Suitable components for the reaction mixture of the disclosed kits may include, but are not limited to, amino acids which optionally may include noncanonical amino acids, NTPs, salts (e.g., sodium salts, potassium salts, and/or magnesium salts), cofactors (e.g., nicotinamide adenine dinucleotide (NAD) and/or coenzyme-A (CoA)), an energy source and optionally an energy source comprising a phosphate group (e.g., ATP or creatine phosphate).

Example One

To date, multiple Biosafety Level-2 ("BSL-2") strains of *Yersinia pestis* ("Yp") have been tested grown at temperatures from 21 to 37° C. *Yersinia* species were cultured to an $OD_{600}$ of ~3.0 and harvested by centrifugation. The harvested cells were resuspended in a formulated buffer system and lysed, and the resulting lysate was clarified by centrifugation, filtered to remove intact cells and other debris, transferred into another buffer system, aliquoted into small tubes, and flash frozen. To enable the lysates to perform transcription and translation, an energy mixture (HEPES pH 8 at 700 mM, ATP at 21 mM, GTP at 21 mM, CTP at 12.6 mM, UTP at 12.6 mM, tRNA at 2.8 mg/ml, CoA at 3.64 mM, NAD at 4.62 mM, cAMP at 10.5 mM, folinic acid at 0.95 mM, Spermidine at 14 mM, and 3-PGA at 420 mM) was also prepared, aliquoted, and flash-frozen in separate tubes. To use the system, tube(s) of lysate and energy mixture were thawed on ice, mixed with a buffer system containing all the canonical amino acids and additional magnesium and potassium as glutamate salts and the "input" DNA, which was then incubated at a temperature between 21 to 37° C. Lysates from different strains were mixed to achieve greater translational throughput. During this incubation, if the input DNA contained the appropriate sequences, the DNA was then transcribed to RNA, and the RNA was translated into a polypeptide.

Genes promoted by a Yp-native promoter for the expression of the gene caf1 were translated in Yp lysates but not in *E. coli* lysates, indicating that the Yp lysates retained some of the unique properties of their source organisms. This makes Yp lysates of obvious interest to researchers working on therapeutics or countermeasures to Yp and those performing basic research on this organism. Additionally, a verified cell-free BSL-2 lysate may enable research on relevant disease-causing strains of Yp with a more favorable safety profile and potentially without the need for a Biosafety level-2 facility.

Yp lysates in some conditions have a higher initial rate of translation than *E. coli* lysates. The mechanisms for this are not yet known but this phenomenon may have substantial implications for sensing applications or detection devices. In sensing applications, the lysates are either used in a transcription or translation platform to detect pathogenic signals from a testing sample or primed with DNA encoding engineered sensing pathways and then exposed to samples which may contain particular threats. There is a lag while the lysate produces the initial sensing machinery, which adds to the total time-to-detect. A Yp lysate with a shorter lag time would produce a faster sensor, which is of paramount importance in military and first-responder applications.

Mixing different strains in some conditions can also increase protein production, likely due to complementation between attenuated strains. This phenomenon may lead to the isolation of components from the strains/lysates that can enhance protein production and could give rise to additional findings.

Example Two

Rapid Initiation of Translation in *Y. pestis:*

Cells were harvested and washed as previously described. The pellet resuspended using 1.025 mL of S30A buffer for every gram of cell mass. The material was passed through a microfluidizer at 15,000 psi, and the lysate was collected in 10 mL increments. Each lysate section was assessed for color and viscosity and the darkest and thickest aliquots were selected for further downstream processing as described previously, except each lysate was subject to its growth temperature during its 90 minutes incubation period. All lysates post dialysis were aliquoted and flash frozen in liquid nitrogen and tested for total protein content using a Bradford assay.

Cell-Free Reactions

All reagents were prepared as described by Sun et al. except for the amino acid 16 mixture which was prepared following Caschera and Noireaux. All reagents were thawed and mixed with the appropriate plasmid DNA to yield the desired deGFP production. For native promoter reactions, p70a-deGFP was propagated in KL740 *E. coli*, isolated using a Zymo II pure Plasmid Plus Midi Kit, and purified using a Zymo DNA clean and concentrate kit. Values were reported in μM of total deGFP content based on a standard curve using purified eGFP (Cell Biolabs, Inc. STA-201).

A black polystyrene microplate was loaded with lysates which were being tested for their ability to produce the 'deGFP' variant of the green fluorescent protein from the p70a promoter. In this experiment, a standard *E. coli* lysate (star markers) was compared to *Y. pestis* lysates sourced from Yp grown at 37° C. (circle markers), 26° C. (plus sign markers), and 21° C. (triangle markers). FIG. 1 shows results from a plate reader fluorescence experiment, such that the Yp lysate produced at 21° C. has a markedly faster initiation of translation and overall superior yield to the other lysates in the experiment.

Example Three

Translation of Genes Using Native Yp Promoters in a Biolayer Interferometry Experiment:

Probes which have been coated with an antibody specific for the F1 antigen were dipped (at ~724 seconds, marked by the first vertical dot-dashed line) into cell-free lysate reactions as described in EXAMPLE TWO. As illustrated in FIG. 2, the lysate reaction conditions in the experiment were an *E. coli* lysate translating the F1 antigen gene driven by a p70a promoter (solid line, triangle markers), an *E. coli* lysate translating the F1 antigen gene driven by the native Yp F1 promoter (solid line, plus sign markers), a *Y. pestis* lysate translating the F1 antigen gene driven by a p70a promoter (dashed line, triangle markers), and a *Y. pestis* lysate translating the F1 antigen gene driven by the native Yp caf1 promoter (dashed line, plus sign markers). Positive sensor response indicated the formation of a complex on the sensor surface, which indicated the presence of the F1 protein. At ~824 seconds, the probes were moved to buffer solution not containing protein to allow bound protein to dissociate, further establishing that the signal was due to the expected reversible antibody: antigen interaction. Expression was evident in all cases except the *E. coli* lysate with the native Yp F1 promoter, indicating that the Yp lysates are capable of producing protein using native Yp promoters while *E. coli* cannot.

Example Four

Protein Expression of Mixes of *Y. pestis* Strains as Shown in Fluorescence Experiment:

A black polystyrene microplate was loaded with lysates produced as described in EXAMPLE TWO, wherein the lysates were being tested for their ability to produce the 'deGFP' variant of the green fluorescent protein from the p70a promoter. In this experiment, lysate sourced from the CO92− strain of *Y. pestis* (triangle markers) was compared to *Y. pestis* lysates sourced from mixes of CO92− with Yp D12 (plus sign markers), Yp Kim6 (circle markers), and Yp EV76 (star markers). The mixture of Yp CO92− and Kim6 lysate exhibited faster initiation of translation and overall superior yield to the other lysate mixtures in the experiment.

REFERENCES

Sun, Z. Z.; Hayes, C. A.; Shin, J.; Caschera, F.; Murray, R. M.; Noireaux, V. Protocols for implementing an *Escherichia coli* based TX-TL cell free expression system for synthetic biology. *J. Visualized Exp.* 2013, 79, 50762.

Caschera, F.; Noireaux, V. Preparation of amino acid mixtures for cell-free expression systems. *BioTechniques* 2015, 58 (1) 40-43.

The invention claimed is:

1. A platform for in vitro transcription of mRNA and/or translation of peptides, polypeptides, or sequence defined polymers, the platform comprising:
   a cell free extract prepared from a cell culture of a species of *Yersinia*, and
   a transcription template, a translation template, or both a transcription template and a translation template.

2. The platform of claim 1, wherein the species of *Yersinia* is *Yersinia pestis*.

3. The platform of claim 1, wherein the species of *Yersinia* is engineered to be deficient in a negative effector for cell-free protein synthesis ("CFPS").

4. The platform of claim 3, wherein the negative effector for CFPS is a selected from the group consisting of a homolog of *E. coli* endA, mazF, rna, rnb, rne, gor, lon, ompT, gdhA, gshA, sdaA, sdaB, speA, WaaL, tnaA, glpK, and any combination thereof.

5. The platform of claim 1, wherein the species of *Yersinia* is engineered to express an upregulated gene product that is a positive effector for CFPS.

6. The platform of claim 5, wherein the positive effector for CFPS is selected from the group consisting of a homolog of *E. coli* ackA, ndk, pykF, cdd, dsbC, dnaK, dnaJ, crpE, tig, groS, groL, infA, infB, fusA, efp, lepA, tufB, hs1R, ffr, and any combination thereof.

7. The platform of claim 1, wherein the species of *Yersinia* has been engineered to express T7 RNA polymerase.

8. The platform of claim 1, wherein the *Yersinia* cell free extract is prepared from cell cultures that are in stationary phase, optionally wherein stationary phase is defined as the cell culture having an OD600 of greater than 3.0.

9. The platform of claim 1, wherein the cell free extract comprises an S12 and/or S30 fraction of the cell culture.

10. The platform of claim 1, further comprising one or more components selected from the group consisting of amino acids, non-canonical amino acids, NTPs, salts, cofactors, an energy source, and an energy source comprising a phosphate group or non-phosphorylated energy group, a translation template, a transcription template, and any combination thereof.

11. The platform of claim 1, further comprising an energy source and optionally an energy source comprising a phosphate group or phosphoenol pyruvate (PEP), wherein the energy source is present at a concentration of greater than 67 mM and less than 100 mM.

12. The platform of claim 1, further comprising a source of potassium (K+), wherein the platform comprises potassium at a concentration greater than 300 mM and less than 500 mM; and/or further comprising a source of magnesium (Mg*), wherein the platform comprises magnesium at a concentration greater than 8 mM, and less than 30 mM.

13. The platform of claim 1, wherein the platform or one or more components of the platform are preserved through freeze-drying.

14. The platform of claim 1, wherein the translation is driven by p70a promoter or a native caf1 promotor.

15. A method for in vitro transcription of mRNA and/or translation of a peptide, a polypeptide, or a sequence defined polymer, the method comprising transcribing a transcription template encoding the mRNA and/or translating in vitro an mRNA encoding the sequence defined polymer, polypeptide, or peptide in the platform of claim 1.

16. The method of claim 15, wherein the method comprises transcribing a DNA template in the platform to provide the translated mRNA.

17. The method of claim 15, wherein the method is performed at a temperature between about 21-37° C.

18. A kit comprising as components: (a) a cell free extract prepared from a cell culture of a species of *Yersinia*; and (b) a reaction mixture for translating an mRNA.

19. The kit of claim 18, wherein the species of *Yersinia* is *Yersinia pestis*.

* * * * *